(12) United States Patent
Rader et al.

(10) Patent No.: US 9,316,646 B2
(45) Date of Patent: Apr. 19, 2016

(54) ANTI-HUMAN ROR1 ANTIBODIES

(75) Inventors: Christoph Rader, Olney, MD (US);
Sivasubramanian Baskar, Elicott City, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 962 days.

(21) Appl. No.: 13/265,582

(22) PCT Filed: Apr. 23, 2010

(86) PCT No.: PCT/US2010/032208
§ 371 (c)(1),
(2), (4) Date: Nov. 14, 2011

(87) PCT Pub. No.: WO2010/124188
PCT Pub. Date: Oct. 28, 2010

(65) Prior Publication Data
US 2012/0058051 A1 Mar. 8, 2012

Related U.S. Application Data

(60) Provisional application No. 61/172,099, filed on Apr. 23, 2009.

(51) Int. Cl.
| | |
|---|---|
| C07K 16/00 | (2006.01) |
| G01N 33/574 | (2006.01) |
| A61K 47/48 | (2006.01) |
| C07K 16/28 | (2006.01) |
| A61K 39/00 | (2006.01) |

(52) U.S. Cl.
CPC .... *G01N 33/57492* (2013.01); *A61K 47/48484* (2013.01); *A61K 47/48561* (2013.01); *C07K 16/2857* (2013.01); *A61K 2039/505* (2013.01); *C07K 2317/569* (2013.01); *G01N 2333/705* (2013.01)

(58) Field of Classification Search
None
See application file for complete search history.

(56) References Cited

U.S. PATENT DOCUMENTS

| | | |
|---|---|---|
| 3,832,253 A | 8/1974 | Di Palma et al. |
| 3,854,480 A | 12/1974 | Zaffaroni |
| 4,452,775 A | 6/1984 | Kent |
| 4,667,014 A | 5/1987 | Nestor et al. |
| 4,748,034 A | 5/1988 | de Rham |
| 5,075,109 A | 12/1991 | Tice et al. |
| 5,843,749 A | 12/1998 | Maisonpierre et al. |
| 7,947,277 B2 | 5/2011 | Ernst et al. |
| 2007/0207510 A1 | 9/2007 | Kipps et al. |

FOREIGN PATENT DOCUMENTS

| | | |
|---|---|---|
| WO | WO 2005/100605 A1 | 10/2005 |
| WO | WO 2007/051077 A2 | 5/2007 |
| WO | WO 2007/146957 A2 | 12/2007 |
| WO | WO 2008/103849 A2 | 8/2008 |
| WO | WO 2008/122039 A2 | 10/2008 |

OTHER PUBLICATIONS

Baskar et al. (Journal of Immunotherapy, vol. 31 No. 9, Nov.-Dec. 2008, p. 969, cited on IDS filed Nov. 14, 2011).*
Rudikoff et al. (Proc Natl Acad Sci USA 1982 vol. 79 p. 1979).*
MacCallum et al. J. Mol. Biol. (1996) 262, 732-745.*
Pascalis et al. (The Journal of Immunology (2002) 169, 3076-3084).*
Casset et al. (BBRC 2003, 307:198-205).*
Vajdos et al. (J. Mol. Biol. (2002) 320, 415-428).*
Chen et al. (J. Mol. Bio. (1999) 293, 865-881).*
Wu et al. (J. Mol. Biol. (1999) 294, 151-162).*
Padlan et al. (PNAS 1989, 86:5938-5942).*
Lamminmaki et al. (JBC 2001, 276:36687-36694).*
Baskar et al., "Unique cell surface expression of receptor tyrosine kinase ROR1 in human B-cell chronic lymphocytic leukemia," *Clin. Cancer Res.*, 14 (2), 396-404 (2008).
Baskar et al., "Targeting human B cell chronic lymphocytic leukemia with a monoclonal antibody specific for the receptor tryrosine kinase ROR1 (Abstract)," *J. Immunother.*, 31 (9), 969 (2008).
Baskar et al., "Targeting human B cell chronic lymphocytic leukemia with a monoclonal antibody specific for the receptor tyrosine kinase ROR1," presented at the 23$^{rd}$ Annual iSBTc Meeting, San Diego, CA, Oct. 31-Nov. 2, 2008.
Broome et al., "Detection of minimal residual disease in chronic lymphicytic leukemia with monoclonal antibodies specific for CD5, CD10, CD19, and ROR1," *Blood* (*ASH Annual Meeting Abstracts*), 112 (Abstract #2079,) (2008).
Carson et al., "Restricted expression of the orphan tyrosine kinase receptor ROR1 in chronic lymphocytic leukemia," *Blood*, 104 (1, part 1, Abstract #772), (2004).
Daneshmanesh et al., "Ror1 a cell surface receptor tyrosine kinase is expressed in chronic lymphocytic leukemia and may serve as a putative target for therapy," *Int. J. Cancer*, 123, 1190-1195 (2008).
Davies et al., "Affinity improvement of single antibody VH domains: residues in all three hypervariable regions affect antigen binding," *Immunotechnology*, 2 (3), 169-179 (1996).
Fukuda et al., "Immune therapy for chronic lymphotcytic leukemia induces the antibocy response against a novel tumor-associated antigen, the orphan tyrposine kinase receptor ROR1," *Blood*, 106 (11, part 1, Abstract #2976), (2005).
Fukuda et al., "Antisera induced by infusions of autologous Ad-CD154-leukemia B cells identify ROR1 as an oncofetal antigen and receptor for Wnt5a," *PNAS*, 105 (8), 3047-3052 (2008).
Gibellini et al., "Receptor tyrosine kinase-like orphan receptor 1 (ROR-1) is expressed in low grade NHL and B-CLL and activates the non canonical Wnt pathway," presented at the 50$^{th}$ Annual American Society of Hematology Meeting, 2008.

(Continued)

*Primary Examiner* — Laura B Goddard
*Assistant Examiner* — Meera Natarajan
(74) *Attorney, Agent, or Firm* — Leydig, Voit & Mayer, Ltd.

(57) ABSTRACT

The invention relates to antibodies having specificity for human ROR1, compositions thereof, and methods for using such antibodies, including in the diagnosis and treatment of disorders associated with aberrant ROR1 expression.

32 Claims, 12 Drawing Sheets

(56) References Cited

OTHER PUBLICATIONS

Hofer et al., "Chimeric rabbit/human Fab and IgG specific for members of the Nogo-66 receptor family selected for species cross-reactivity with an improved phage display vector," *J. Immunol. Methods*, 318 (1-2), 75-87 (2007).

Holt et al., "Domain antibodies: proteins for therapy," *Trends Biotechnol.*, 21 (11), 484-490 (2003).

International Search Report, Application No. PCT/US2010/032208, dated Jul. 6, 2010.

Klein et al., "Gene expression profiling of B cell chronic lymphocytic leukemia reveals a homogeneous phenotype related to memory B cells," *J. Exp. Med.*, 194 (11), 1625-1638 (2001).

Kreitman et al., "Making fusion toxins to target leukemia and lymphoma," *Methods in Molecular Medicine, 25, Drug Targeting*, Francis et al., eds., 215-226, Humana Press, Inc., New Jersey (2000).

Little et al., "Of mice and men: hybridoma and recombinant antibodies," *Immunology Today*, 21 (8), 364-370 (2000).

Marcu-Malina et al., "Re-targeting T-cells against cancer by gene-transfer of tumor-reactive receptors," *Expert Opin. Biol. Ther.*, 9 (5), 579-591 (2009).

Masiakowski et al., "A novel family of cell surface receptors with tyrosine kinase-like domain," *J. Biol. Chem.*, 267 (36), 26181-26190 (1992).

Morrison, "Cloning, expression, and modification of antibody V regions," *Current Protocols in Immunology, Supplement 47* (Unit 2.12), 2.12.1-2.12.17 (2002).

Pastan et al., "Recombinant immunotoxins in the treatment of cancer," *Methods in Molecular Biology*, 248, 503-518 (2002).

Rader et al., "Integrin $\alpha(v)\beta3$ targeted therapy for Kaposi's sarcoma with an in vitro evolved antibody," *FASEB J.*, 16 (14), 2000-2002 (2002).

Rosenwald et al., "Relation of gene expression phenotype to immunoglobulin mutation genotype in B cell chronic lymphocytic leukemia," *J. Exp. Med.*, 194 (11), 1639-1647 (2001).

Russell et al., "Structural features can be unconserved in proteins with similar folds. An analysis of side-chain to side-chain contacts secondary structure and accessibility," *J. Mol. Biol.*, 244 (3), 332-350 (1994).

Written Opinion of the International Searching Authority, Application No. PCT/US2010/032208, dated Jul. 6, 2010.

Wu et al., "Arming antibodies: prospects and challenges for immunoconjugates," *Nat. Biotechnol.*, 23 (9), 1137-1146 (2005).

\* cited by examiner

ROR1-ECD

~ 50 kDa

Fc-ROR1

~150 kDa (dimer)
~ 75 kDa (monomer)

Control 1 - 1 µg/mL (IgG) polyclonal mouse IgG
Control 2 - goat anti-mouse IgG polyclonal antibody-FITC
A - 1 µg/mL (~6.5 nM) mAb 2A2
B - 0.1 µg/mL (~650 pM) mAb 2A2
C - 0.01 µg/mL (~65 pM) ) mAb 2A2
D - 0.001 µg/mL (~6.5 pM) mAb 2A2 mAb 2A2 (VH)

```
1   QVQLQQSGAELVRPGASVTLSCKASGYTFSDYEMHWVIQT
41  PVHGLEWIGAIDPETGGTAYNQKFKGKAILTADKSSSTAY
81  MELRSLTSEDSAVYYCTGYYDYDSFTYWGQGTLVTVSA  (SEQ ID NO:1)
```

- FR1    QVQLQQSGAELVRPGASVTLSCKASGYTFS (SEQ ID NO:3)
- CDR1   DYEMH (SEQ ID NO:4)
- FR2    WVIQTPVHGLEWIG (SEQ ID NO:5)
- CDR2   AIDPETGGTAYNQKFKG (SEQ ID NO:6)
- FR3    KAILTADKSSSTAYMELRSLTSEDSAVYYCTG (SEQ ID NO:7)
- CDR3   YYDYDSFTY (SEQ ID NO:8)
- FR4    WGQGTLVTVSA (SEQ ID NO:9)

mAb 2A2 (VL)

```
1   DIVMTQSQKIMSTTVGDRVSITCKASQNVDAAVAWYQQKP
41  GQSPKLLIYSASNRYTGVPDRFTGSGSGTDFTLTISNMQS
81  EDLADYFCQQYDIYPYTFGGGTKLEIK   (SEQ ID NO:2)
```

- FR1    DIVMTQSQKIMSTTVGDRVSITC (SEQ ID NO:10)
- CDR1   KASQNVDAAVA (SEQ ID NO:11)
- FR2    WYQQKPGQSPKLLIY (SEQ ID NO:12)
- CDR2   SASNRYT (SEQ ID NO:13)
- FR3    GVPDRFTGSGSGTDFTLTISNMQSEDLADYFC (SEQ ID NO:14)
- CDR3   QQYDIYPYT (SEQ ID NO:15)
- FR4    FGGGTKLEIK (SEQ ID NO:16)

Figure 5

2A2 VH (heavy chain variable domain)

Original DNA sequence:
CAGGTTCAACTGCAGCAGTCTGGGGCTGAGCTGGTGAGGCCTGGGGCTTCAGTGACG
CTGTCCTGCAAGGCTTCGGGCTACACATTTTCTGACTATGAAATGCACTGGGTGATT
CAGACACCTGTGCATGGCCTGGAATGGATTGGAGCTATTGATCCTGAAACTGGTGGT
ACTGCCTACAATCAGAAGTTCAAGGGCAAGGCCATACTGACTGCAGACAAATCCTCC
AGCACAGCCTACATGGAGCTCCGCAGCCTGACATCTGAGGACTCTGCCGTCTATTAC
TGTACAGGCTACTATGATTACGACTCGTTTACTTACTGGGGCCAAGGGACTCTGGTC
ACTGTCTCTGCA (SEQ ID NO: 17)

Optimized DNA sequence for mammalian expression:
CAAGTGCAGCTTCAACAGTCTGGGGCAGAACTCGTAAGACCAGGAGCATCAGTGACA
CTGTCTTGTAAAGCCTCCGGCTATACCTTCTCTGACTACGAGATGCATTGGGTCATC
CAGACACCAGTACATGGGCTCGAATGGATAGGAGCCATAGATCCAGAGACAGGCGGA
ACAGCATACAACCAGAAGTTCAAAGGCAAGGCCATTCTCACAGCGGACAAGAGCAGT
AGCACCGCTTACATGGAGTTGCGATCCCTGACCAGTGAGGACTCTGCAGTCTACTAT
TGTACAGGGTACTATGACTACGACTCATTCACATATTGGGGGCAGGGTACCTTGGTG
ACTGTCTCCGCT (SEQ ID NO: 18)

2A2 VL (kappa light chain variable domain)

Original DNA sequence:
GACATTGTGATGACCCAGTCTCAAAAAATCATGTCCACAACAGTGGGAGACAGGGTC
AGCATCACCTGCAAGGCCAGTCAGAATGTGGATGCTGCTGTAGCCTGGTATCAACAG
AAACCAGGACAATCTCCTAAACTACTGATTTACTCAGCATCCAATCGGTACACTGGA
GTCCCTGATCGCTTCACAGGCAGTGGATCTGGGACAGATTTCACTCTCACCATTAGC
AATATGCAGTCTGAAGACCTGGCAGATTATTTCTGTCAGCAATATGACATCTATCCG
TACACGTTCGGAGGGGGGACCAAGCTGGAAATAAAA (SEQ ID NO: 19)

Optimized DNA sequence for mammalian expression:
GATATAGTGATGACGCAGTCCCAGAAGATCATGTCCACGACCGTCGGGGATCGGGTC
AGTATAACATGTAAGGCATCCCAGAACGTGGACGCGGCCGTGGCTTGGTATCAACAG
AAACCCGGTCAATCCCCAAAGCTCCTCATCTACTCTGCGAGCAATAGATATACCGGT
GTGCCTGATAGGTTCACCGGAAGCGGATCCGGAACAGATTTCACCCTGACTATCAGC
AATATGCAATCCGAGGACTTGGCTGACTACTTTTGCCAGCAATACGACATATACCCC
TACACCTTCGGCGGAGGCACAAAGCTCGAGATAAAG (SEQ ID NO: 20)

Figure 6

SEQUENCE LISTING

```
<160> NUMBER OF SEQ ID NOS: 20

<210> SEQ ID NO 1
<211> LENGTH: 118
<212> TYPE: PRT
<213> ORGANISM: Artificial Sequence
<220> FEATURE:
<223> OTHER INFORMATION: Antibody fragment dervied from Mus musculus
      hybridoma

<400> SEQUENCE: 1

Gln Val Gln Leu Gln Gln Ser Gly Ala Glu Leu Val Arg Pro Gly Ala
1               5                   10                  15

Ser Val Thr Leu Ser Cys Lys Ala Ser Gly Tyr Thr Phe Ser Asp Tyr
            20                  25                  30

Glu Met His Trp Val Ile Gln Thr Pro Val His Gly Leu Glu Trp Ile
        35                  40                  45

Gly Ala Ile Asp Pro Glu Thr Gly Gly Thr Ala Tyr Asn Gln Lys Phe
    50                  55                  60

Lys Gly Lys Ala Ile Leu Thr Ala Asp Lys Ser Ser Ser Thr Ala Tyr
```

```
                65                  70                  75                  80
Met Glu Leu Arg Ser Leu Thr Ser Glu Asp Ser Ala Val Tyr Tyr Cys
                    85                  90                  95

Thr Gly Tyr Tyr Asp Tyr Asp Ser Phe Thr Tyr Trp Gly Gln Gly Thr
                100                 105                 110

Leu Val Thr Val Ser Ala
        115

<210> SEQ ID NO 2
<211> LENGTH: 107
<212> TYPE: PRT
<213> ORGANISM: Artificial Sequence
<220> FEATURE:
<223> OTHER INFORMATION: Antibody fragment derived from Mus musculus
      hybridoma

<400> SEQUENCE: 2

Asp Ile Val Met Thr Gln Ser Gln Lys Ile Met Ser Thr Thr Val Gly
1               5                   10                  15

Asp Arg Val Ser Ile Thr Cys Lys Ala Ser Gln Asn Val Asp Ala Ala
                20                  25                  30

Val Ala Trp Tyr Gln Gln Lys Pro Gly Gln Ser Pro Lys Leu Leu Ile
            35                  40                  45

Tyr Ser Ala Ser Asn Arg Tyr Thr Gly Val Pro Asp Arg Phe Thr Gly
    50                  55                  60

Ser Gly Ser Gly Thr Asp Phe Thr Leu Thr Ile Ser Asn Met Gln Ser
65                  70                  75                  80

Glu Asp Leu Ala Asp Tyr Phe Cys Gln Gln Tyr Asp Ile Tyr Pro Tyr
                85                  90                  95

Thr Phe Gly Gly Gly Thr Lys Leu Glu Ile Lys
                100                 105

<210> SEQ ID NO 3
<211> LENGTH: 30
<212> TYPE: PRT
<213> ORGANISM: Artificial Sequence
<220> FEATURE:
<223> OTHER INFORMATION: Antibody fragment derived from Mus musculus
      hybridoma

<400> SEQUENCE: 3

Gln Val Gln Leu Gln Gln Ser Gly Ala Glu Leu Val Arg Pro Gly Ala
1               5                   10                  15

Ser Val Thr Leu Ser Cys Lys Ala Ser Gly Tyr Thr Phe Ser
                20                  25                  30

<210> SEQ ID NO 4
<211> LENGTH: 5
<212> TYPE: PRT
<213> ORGANISM: Artificial Sequence
<220> FEATURE:
<223> OTHER INFORMATION: Antibody fragment derived from Mus musculus
      hybridoma

<400> SEQUENCE: 4

Asp Tyr Glu Met His
1               5

<210> SEQ ID NO 5
<211> LENGTH: 14
<212> TYPE: PRT
<213> ORGANISM: Artificial Sequence
```

```
<220> FEATURE:
<223> OTHER INFORMATION: Antibody fragment derived from Mus musculus
      hybridoma

<400> SEQUENCE: 5

Trp Val Ile Gln Thr Pro Val His Gly Leu Glu Trp Ile Gly
1               5                   10

<210> SEQ ID NO 6
<211> LENGTH: 17
<212> TYPE: PRT
<213> ORGANISM: Artificial Sequence
<220> FEATURE:
<223> OTHER INFORMATION: Antibody fragment derived from Mus musculus
      hybridoma

<400> SEQUENCE: 6

Ala Ile Asp Pro Glu Thr Gly Gly Thr Ala Tyr Asn Gln Lys Phe Lys
1               5                   10                  15

Gly

<210> SEQ ID NO 7
<211> LENGTH: 32
<212> TYPE: PRT
<213> ORGANISM: Artificial Sequence
<220> FEATURE:
<223> OTHER INFORMATION: Antibody fragment derived from Mus musculus
      hybridoma

<400> SEQUENCE: 7

Lys Ala Ile Leu Thr Ala Asp Lys Ser Ser Thr Ala Tyr Met Glu
1               5                   10                  15

Leu Arg Ser Leu Thr Ser Glu Asp Ser Ala Val Tyr Tyr Cys Thr Gly
            20                  25                  30

<210> SEQ ID NO 8
<211> LENGTH: 9
<212> TYPE: PRT
<213> ORGANISM: Artificial Sequence
<220> FEATURE:
<223> OTHER INFORMATION: Antibody fragment derived from Mus musculu
      hybridoma

<400> SEQUENCE: 8

Tyr Tyr Asp Tyr Asp Ser Phe Thr Tyr
1               5

<210> SEQ ID NO 9
<211> LENGTH: 11
<212> TYPE: PRT
<213> ORGANISM: Artificial Sequence
<220> FEATURE:
<223> OTHER INFORMATION: Antibody fragment derived from Mus musculu
      hybridoma

<400> SEQUENCE: 9

Trp Gly Gln Gly Thr Leu Val Thr Val Ser Ala
1               5                   10

<210> SEQ ID NO 10
<211> LENGTH: 23
<212> TYPE: PRT
<213> ORGANISM: Artificial Sequence
<220> FEATURE:
<223> OTHER INFORMATION: Antibody fragment derived from Mus musculus
      hybridoma
```

```
<400> SEQUENCE: 10

Asp Ile Val Met Thr Gln Ser Gln Lys Ile Met Ser Thr Thr Val Gly
1               5                   10                  15

Asp Arg Val Ser Ile Thr Cys
            20

<210> SEQ ID NO 11
<211> LENGTH: 11
<212> TYPE: PRT
<213> ORGANISM: Artificial Sequence
<220> FEATURE:
<223> OTHER INFORMATION: Antibody fragment derived from Mus musculus
      hybridoma

<400> SEQUENCE: 11

Lys Ala Ser Gln Asn Val Asp Ala Ala Val Ala
1               5                   10

<210> SEQ ID NO 12
<211> LENGTH: 15
<212> TYPE: PRT
<213> ORGANISM: Artificial Sequence
<220> FEATURE:
<223> OTHER INFORMATION: Antibody fragment derived from Mus musculus
      hybridoma

<400> SEQUENCE: 12

Trp Tyr Gln Gln Lys Pro Gly Gln Ser Pro Lys Leu Leu Ile Tyr
1               5                   10                  15

<210> SEQ ID NO 13
<211> LENGTH: 7
<212> TYPE: PRT
<213> ORGANISM: Artificial Sequence
<220> FEATURE:
<223> OTHER INFORMATION: Antibody fragment derived from Mus musculus
      hybridoma

<400> SEQUENCE: 13

Ser Ala Ser Asn Arg Tyr Thr
1               5

<210> SEQ ID NO 14
<211> LENGTH: 32
<212> TYPE: PRT
<213> ORGANISM: Artificial Sequence
<220> FEATURE:
<223> OTHER INFORMATION: Antibody fragment derived from Mus musculus
      hybridoma

<400> SEQUENCE: 14

Gly Val Pro Asp Arg Phe Thr Gly Ser Gly Ser Gly Thr Asp Phe Thr
1               5                   10                  15

Leu Thr Ile Ser Asn Met Gln Ser Glu Asp Leu Ala Asp Tyr Phe Cys
            20                  25                  30

<210> SEQ ID NO 15
<211> LENGTH: 9
<212> TYPE: PRT
<213> ORGANISM: Artificial Sequence
<220> FEATURE:
<223> OTHER INFORMATION: Antibody fragment derived from Mus musculus
      hybridoma

<400> SEQUENCE: 15

Gln Gln Tyr Asp Ile Tyr Pro Tyr Thr
```

<210> SEQ ID NO 16
<211> LENGTH: 10
<212> TYPE: PRT
<213> ORGANISM: Artificial Sequence
<220> FEATURE:
<223> OTHER INFORMATION: Antibody fragment derived from Mus musculus hybridoma

<400> SEQUENCE: 16

Phe Gly Gly Gly Thr Lys Leu Glu Ile Lys
1               5                   10

<210> SEQ ID NO 17
<211> LENGTH: 354
<212> TYPE: DNA
<213> ORGANISM: Artificial Sequence
<220> FEATURE:
<223> OTHER INFORMATION: cDNA derived from Mus musculus hybridoma

<400> SEQUENCE: 17
caggttcaac tgcagcagtc tggggctgag ctggtgaggc ctggggcttc agtgacgctg      60
tcctgcaagg cttcgggcta cacatttttct gactatgaaa tgcactgggt gattcagaca    120
cctgtgcatg gcctggaatg gattggagct attgatcctg aaactggtgg tactgcctac    180
aatcagaagt tcaagggcaa ggccatactg actgcagaca atcctccag cacagcctac     240 atggagctcc gcagcctgac atctgaggac tctgccgtct attactgtac aggctactat    300
gattacgact cgtttactta ctggggccaa gggactctgg tcactgtctc tgca           354

<210> SEQ ID NO 18
<211> LENGTH: 354
<212> TYPE: DNA
<213> ORGANISM: Artificial Sequence
<220> FEATURE:
<223> OTHER INFORMATION: Optimized sequence for mammalian expression system

<400> SEQUENCE: 18
caagtgcagc ttcaacagtc tggggcagaa ctcgtaagac caggagcatc agtgacactg      60
tcttgtaaag cctccggcta taccttctct gactacgaga tgcattgggt catccagaca    120
ccagtacatg gctcgaatg gataggagcc atagatccag agacaggcgg aacagcatac     180
aaccagaagt tcaaaggcaa ggccattctc acagcggaca gagcagtag caccgcttac     240 atggagttgc gatccctgac cagtgaggac tctgcagtct actattgtac agggtactat    300
gactacgact cattcacata ttgggggcag ggtaccttgg tgactgtctc cgct            354

<210> SEQ ID NO 19
<211> LENGTH: 321
<212> TYPE: DNA
<213> ORGANISM: Artificial Sequence
<220> FEATURE:
<223> OTHER INFORMATION: cDNA derived from Mus musculus hybridoma

<400> SEQUENCE: 19
gacattgtga tgacccagtc tcaaaaaatc atgtccacaa cagtgggaga cagggtcagc      60
atcacctgca aggccagtca gaatgtggat gctgctgtag cctggtatca acagaaacca    120
ggacaatctc ctaaactact gatttactca gcatccaatc ggtacactgg agtccctgat    180
cgcttcacag gcagtggatc tgggacagat ttcactctca ccattagcaa tatgcagtct    240

```
gaagacctgg cagattattt ctgtcagcaa tatgacatct atccgtacac gttcggaggg    300
gggaccaagc tggaaataaa a                                              321

<210> SEQ ID NO 20
<211> LENGTH: 321
<212> TYPE: DNA
<213> ORGANISM: Artificial Sequence
<220> FEATURE:
<223> OTHER INFORMATION: Optimized sequence for mammalian expression
      system

<400> SEQUENCE: 20
gatatagtga tgacgcagtc ccagaagatc atgtccacga ccgtcgggga tcgggtcagt     60
ataacatgta aggcatccca gaacgtggac gcggccgtgg cttggtatca acagaaaccc    120
ggtcaatccc caaagctcct catctactct gcgagcaata gatataccgg tgtgcctgat    180
aggttcaccg gaagcggatc cggaacagat ttcaccctga ctatcagcaa tatgcaatcc    240
gaggacttgg ctgactactt ttgccagcaa tacgacatat acccctacac cttcggcgga    300
ggcacaaagc tcgagataaa g                                              321
```

ANTI-HUMAN ROR1 ANTIBODIES

CROSS-REFERENCE TO RELATED APPLICATIONS

This patent application is a U.S. National Phase of International Patent Application No. PCT/US10/32208, filed Apr. 23, 2010, which claims the benefit of U.S. Provisional Patent Application No. 61/172,099, filed Apr. 23, 2009, which is are incorporated by reference in their entireties.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 8,948 Byte ASCII (Text) file named "708950ST25.TXT," created on Sep. 27, 2011.
Applicants respectfully request entry into the specification of the Sequence listing submitted herewith.

BACKGROUND OF THE INVENTION

Antibody therapies and diagnostics have been developed for use in treating a wide range of conditions including autoimmune diseases or disorders, infectious diseases, and cancers. Such therapies are useful but also can be associated with undesirable immunogenicity and can damage healthy cells and tissues.

B-cell chronic lymphocytic leukemia (B-CLL) and and mantle cell lymphoma (MCL) are two incurable forms of B-cell lymphoma with a combined incidence of new cases that exceeds 18,000 patients per year in the United States alone. Antibody therapies that have been developed for B cell lymphomas, which include rituximab, a chimeric monoclonal antibody (mAb), and alemtuzumab, a humanized mAb. However, the target antigens for both of these drugs (CD20 and CD52, respectively) are expressed not only in malignant B cells but also in normal B cells, and CD52 is ubiquitously expressed on a variety of normal cells of the immune system. Therefore, immunosuppression can be a concern with these antibody therapies. Currently in the United States and Europe, there is no commercial therapeutic antibody that specifically recognizes an antigen present on malignant B cells, but not on normal B cells.

There is a desire for additional therapeutic and diagnostic antibodies having good efficacy and that exhibit minimal binding and/or damage to non-diseased cells.

BRIEF SUMMARY OF THE INVENTION

The invention provides an isolated antibody with specificity for the extracellular domain of receptor tyrosine kinase-like orphan receptor 1 (ROR 1), which is selectively expressed on the surface of malignant cells, including B-cell tumors and other cancers.

In particular, the invention provides an isolated antibody having specificity for human ROR1 and having (a) a heavy chain with at least 90% identity to a sequence selected from the group consisting of SEQ ID NO: 1, (b) a light chain with at least 90% identity to a sequence selected from the group consisting of SEQ ID NO: 2; or (c) both a heavy chain of (a) and a light chain of (b).

The invention also provides an isolated antibody having specificity for human ROR1 and having at least one CDR that includes a sequence selected from the group consisting of SEQ ID NO:4, SEQ ID NO:6, SEQ ID NO:8, SEQ ID NO: 11, SEQ ID NO: 13, and SEQ ID NO: 15. In other embodiments, the isolated antibody can include one or more variants of the foregoing CDRs which have 1, 2 or 3 amino acid substitutions, insertions, or deletions.

The invention further provides a pharmaceutical composition comprising an antibody of the invention and a pharmaceutically acceptable carrier.

In addition, the invention provides a method of treating a disease or condition associated with elevated expression of ROR1 (e.g., a B-cell lymphoma, renal cell carcinoma, colon cancer, or breast cancer) by administering a therapeutically effective amount of an isolated antibody of the invention or a pharmaceutical composition thereof to a subject in need thereof.

The antibodies and compositions of the invention can also be used in diagnostic methods to detect cells with altered levels of ROR1, e.g., in a sample or in a subject.

BRIEF DESCRIPTION OF THE DRAWING(S)

Figure 4:
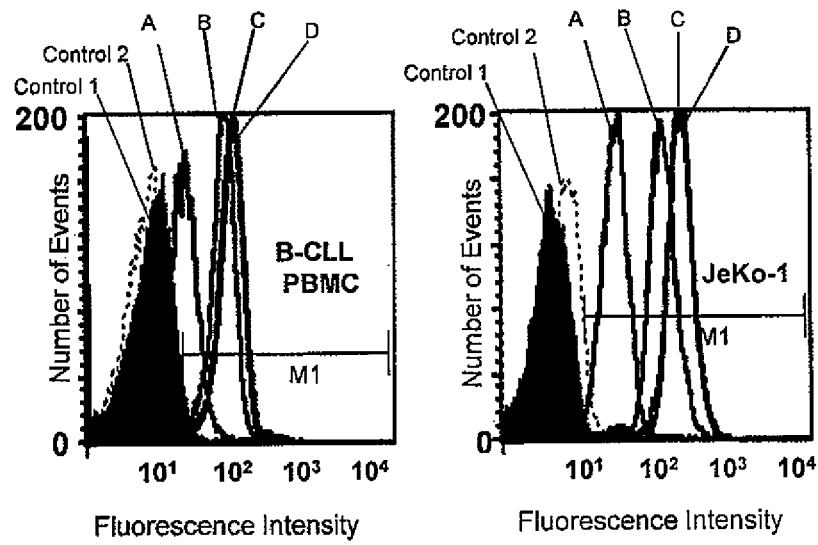

FIG. 4 is a pair of histogram panels depicting the results of fluorescence activated cell sorting (FACS) analysis evaluating mAB 2A2 binding to peripheral blood mononuclear cells (PBMC) taken from B-CLL patients (first panel) and cultured JeKo-1 cells (second panel) in terms of the number of events versus fluorescence intensity for (A) 1 µg/mL (~6.5 nM) mAb 2A2, (B) 0.1 µg/mL (~650 pM) mAb 2A2, (C) 0.01 µg/mL (~65 pM) mAb 2A2, and (D) 0.001 µg/mL (~6.5 pM) mAb 2A2, with 1 µg/mL polyclonal mouse IgG (solid black histogram) and goat anti-mouse IgG polyclonal antibody conjugated to fluorescein isothiocyanate (FITC) (broken line histogram) as controls.

FIG. 5 is a list of the amino acid sequences corresponding to the mAb 2A2 variable region heavy chain (VH) (SEQ ID NO: 1), light chain (VL) (SEQ ID NO: 2), VH framework regions FR1-FR4 (SEQ ID NOs: 3, 5, 7, and 9), VH complementarity determining regions CDR1-3 (SEQ ID NOs: 4, 6, and 8), VL FR1-FR4 (SEQ ID NOs: 10, 12, 14, and 16), and VL CDR1-CDR3 (SEQ ID NOs: 11, 13, and 15) regions.

FIG. 6 is a list of DNA coding sequences corresponding to the "original" VH (SEQ ID NO: 17) and VL (SEQ ID NO: 19) cDNAs isolated from mAb 2A2 and their respective VH (SEQ ID NO: 18) and VL (SEQ ID NO: 20) coding sequences optimized for expression in a mammalian system.

Figure 7A:
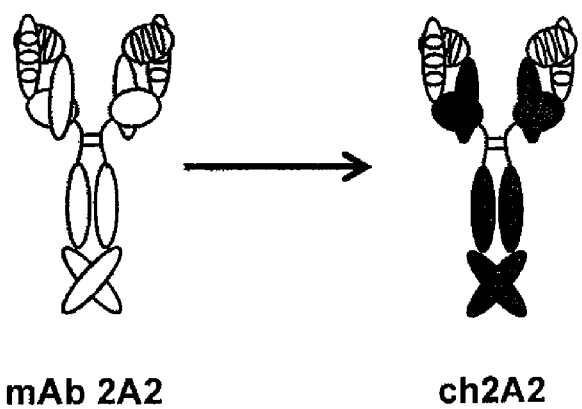

FIG. 7A is a schematic that depicts mAb 2A2, including its constant and variable regions (no fill), and a chimeric antibody (ch2A2), that included human constant regions (dark fill) and mouse mAb 2A2 variable region (no fill).

Figure 7B:
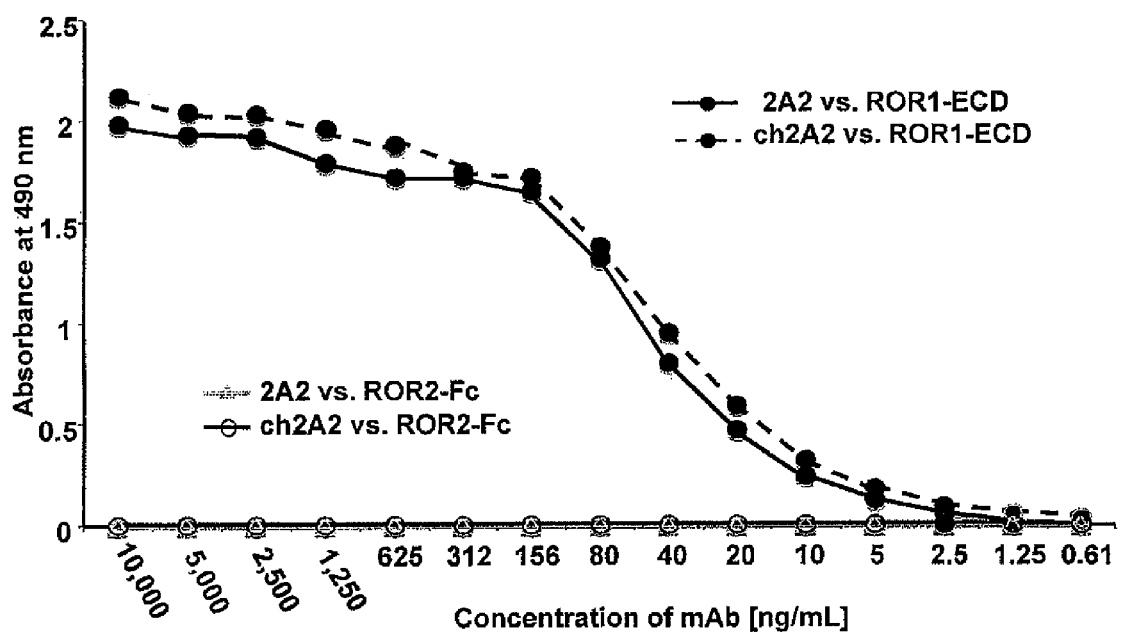

FIG. 7B is a graph that depicts the results of ELISA studies comparing mAb 2A2 and ch2A2 binding to ROR1 ECD (as well as binding to ROR2) as a function of antibody concentration.

Figure 8:
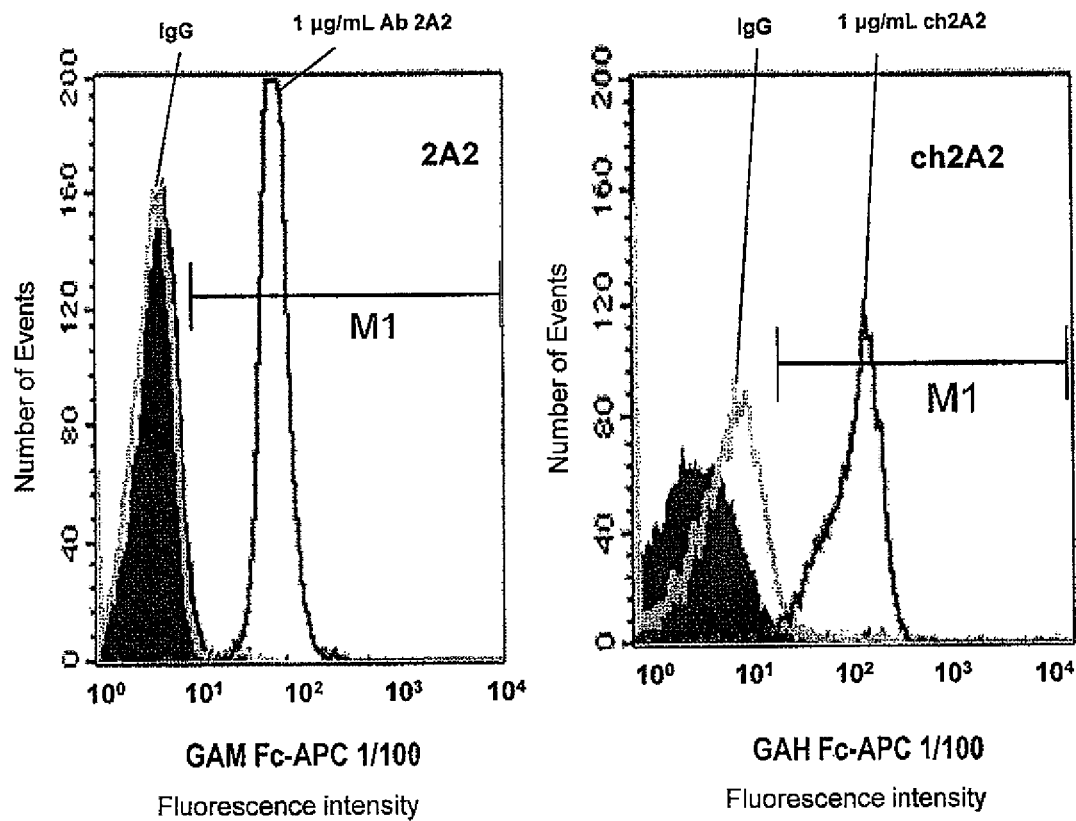

FIG. 8 is a pair of histogram panels depicting the results of FACS analysis evaluating mAb 2A2 (first panel) and ch2A2 (second panel) binding to JeKo-1 cells.

Figure 9:
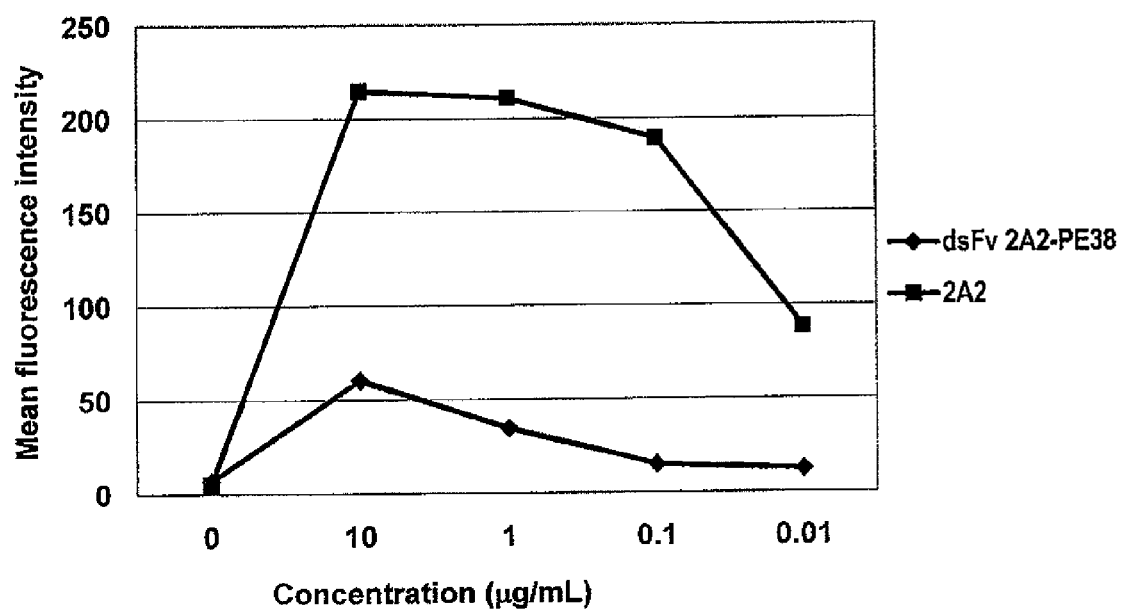

FIG. 9 is a graph that depicts the results of a flow cytometry assay comparing dsFv 2A2-PE38 immunotoxin and mAb 2A2 with respect to the ability to bind to JeKo-1 cells in terms of fluorescence intensity of labeling antibody as a function of dsFv 2A2-PE38 and mAb 2A2 concentration.

Figure 10:
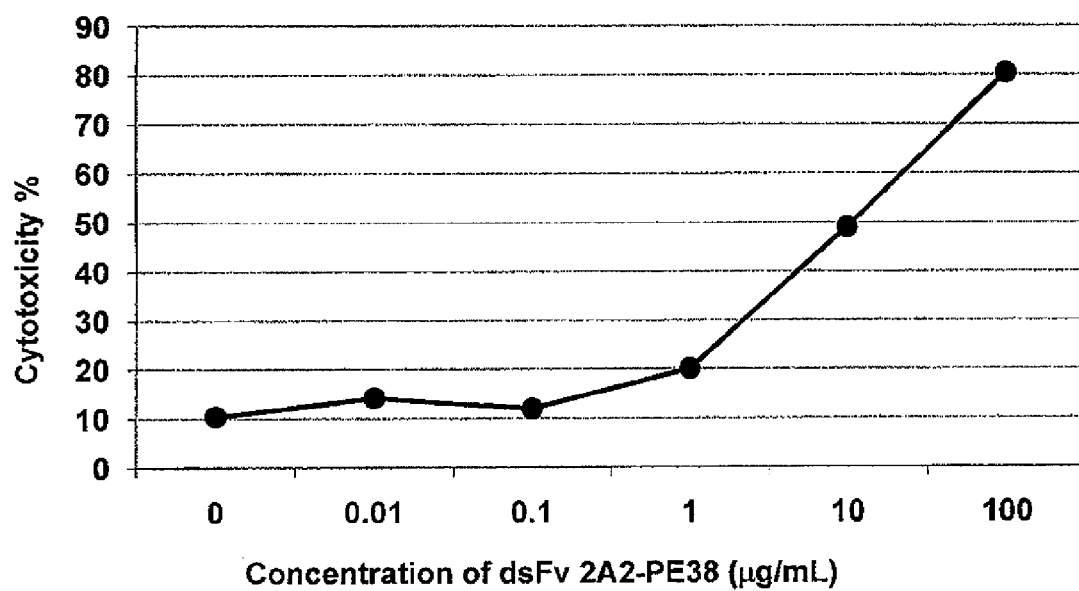

FIG. 10 is a graph that depicts the results of a cytotoxicity assay in terms of cytotoxicity % (of cells) as a function of dsFv 2A2-PE38 concentration.

Figure 11:
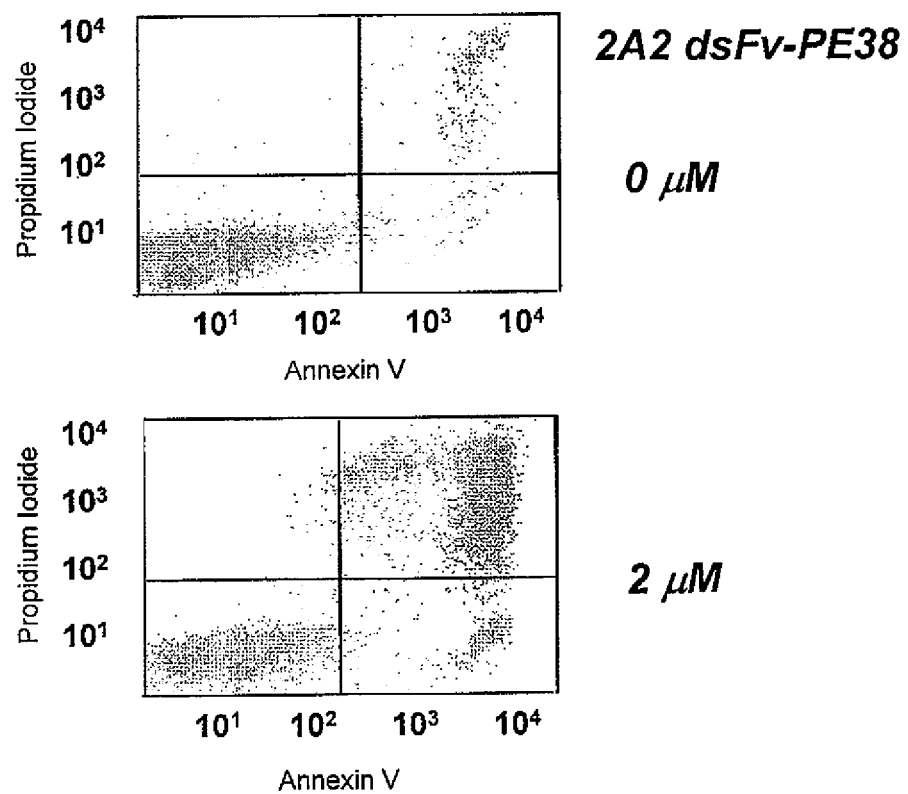

FIG. 11 is a dot plot depicting the results of apoptosis analysis in terms of annexin V and propidium iodide signal for 2 µM dsFv 2A2-PE38 as applied to JeKo-1 cells.

Figure 12:
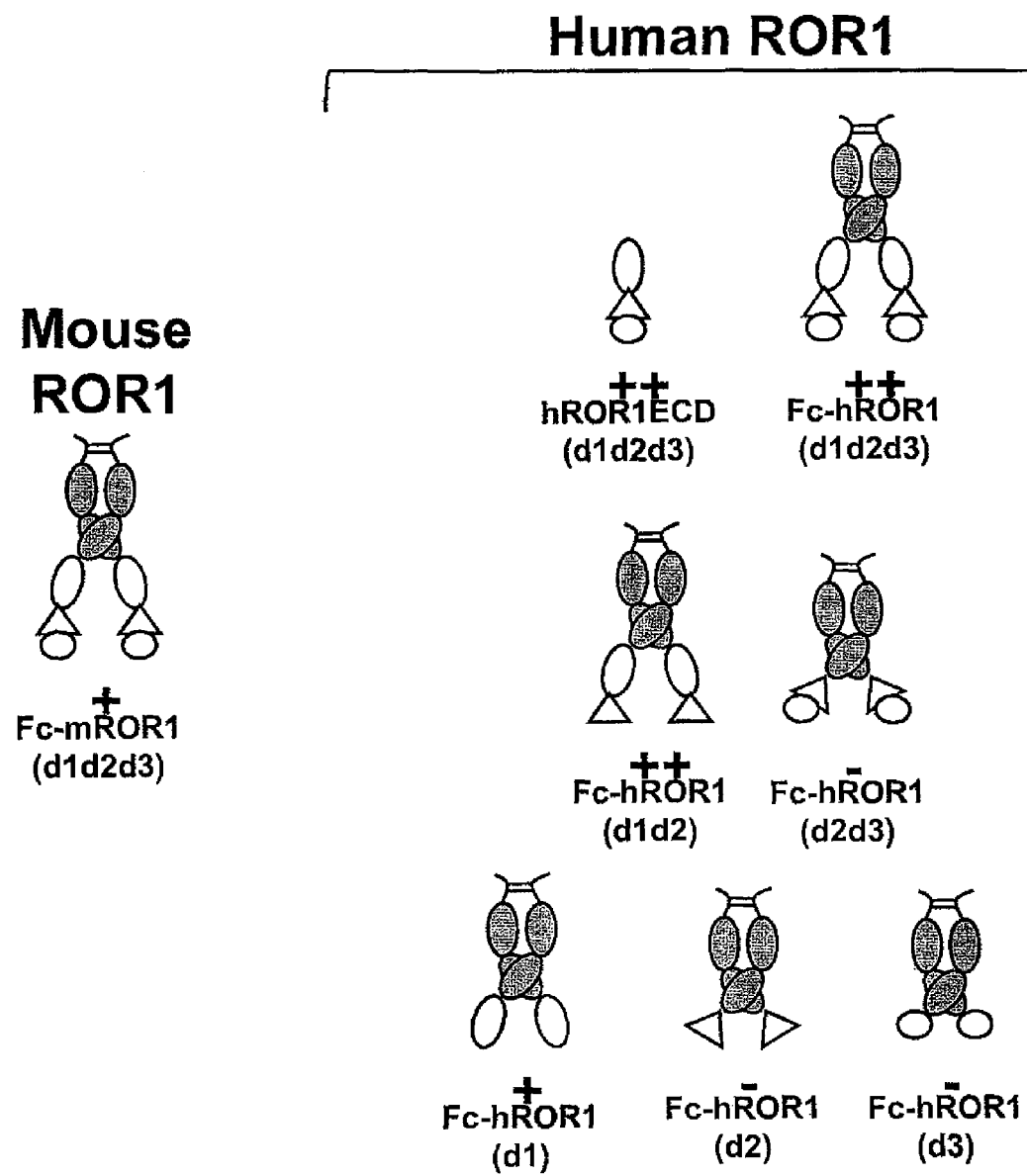

FIG. 12 is a schematic depiction of ELISA of mAb 2A2 binding to various hROR-1 extracellular domain constructs, with murine ROR1 as a control.

DETAILED DESCRIPTION OF THE INVENTION

Receptor tyrosine kinase-like orphan receptor 1 (ROR1) is a conserved embryonic protein whose expression becomes progressively reduced during embryonic development in mammals. The intact protein, including its extracellular domain, does not appear to be significantly expressed in normal, adult mammalian tissues. In particular, studies have not identified significant expression of ROR1 on the cell surface of normal adult human tissues, including normal B cells. Baskar et al., *Clin. Cancer Res.*, 14: 396-404 (2008), Danesh-Manesh et al., *Int. J. Cancer*, 123: 1190-1195 (2008), and Fukuda et al., *Proc. Nat'l. Acad. Sci.* USA, 105: 3047-3052 (2008). However, ROR1 is expressed on the cell surface of malignant B-cells, including B-cell chronic lymphocytic leukemia (B-CLL) and mantle cell lymphoma (MCL). It has also been reported that ROR1 is expressed in certain other cancer cell lines including Burkett's lymphoma, renal cell carcinoma, colon cancer, and breast cancer. U.S. Patent Application Publ. 2007/0207510. Therefore, ROR1 can be considered a selective marker for these cancers. The invention provides an antibody to this selective marker.

In particular, the invention provides an antibody having specificity for ROR1, comprising (a) a heavy chain having at least 90% identity to SEQ ID NO: 1; (b) a light chain variable domain having at least 90% sequence identity to SEQ ID NO: 2; or (c) both a heavy chain of (a) and a light chain of (b). In a preferred embodiment, the antibody comprises both a heavy chain of (a) and a light chain of (b).

The antibody can be an isolated antibody having specificity for human ROR1, wherein the antibody comprises a heavy chain having at least 90% identity to a sequence such as SEQ ID NO: 1. In other embodiments, the percentage identity can be at least 91%, at least 92%, at least 93%, at least 94%, at least 95%, at least 96%, at least 97%, at least 98%, or at least 99%, or even 100%. In preferred embodiments, the heavy chain has at least 95% identity to SEQ ID NO: 1. In more preferred embodiments, the heavy chain has 100% identity to SEQ ID NO: 1.

The antibody can be an isolated antibody having specificity for human ROR1, wherein the antibody comprises a light chain having at least 90% identity to a sequence such as SEQ ID NO: 2. In other embodiments, the percentage identity can be at least 91%, at least 92%, at least 93%, at least 94%, at least 95%, at least 96%, at least 97%, at least 98%, or at least 99%, or even 100%. In preferred embodiments, the light chain has at least 95% identity to SEQ ID NO: 2. In more preferred embodiments, the light chain has 100% identity to SEQ ID NO: 2.

In some embodiments, the antibody can comprise any heavy chain as described above, in combination with any suitable light chain, such as those described above. Likewise, the antibody can comprise any of the light chains as described above in combination with any suitable heavy chain, such as those described above. For example, in preferred embodiments, the antibody comprises a heavy chain having at least 90% identity to SEQ ID NO: 1 and a light chain having at least 90% identity to SEQ ID NO: 2. In a preferred embodiment, the antibody comprises the heavy chain of SEQ ID NO: 1 and the light chain of SEQ ID NO: 2.

Percent (%) identity of peptide sequences can be calculated, for example, as $100 \times [(\text{identical positions})/\min(TG_A, TG_B)]$, where $TG_A$ and $TG_B$ are the sum of the number of residues and internal gap positions in peptide sequences A and B in the alignment that minimizes $TG_A$ and $TG_B$. See, e.g., Russell et al., *J. Mol Biol.*, 244: 332-350 (1994).

The antibody of the invention can be any antibody including a full length antibody or an antibody fragment. The antibody can be polyclonal, monoclonal, recombinant, chimeric, or humanized. Furthermore, the antibody can be of any isotype including without limitation IgA, IgD, IgE, IgG, or IgM. Thus, for example, the antibody can be any IgA such as IgA1 or IgA2, or any IgG such as IgG1, IgG2, IgG3, IgG4, or synthetic IgG. The antibody can also be any antibody fragment having specificity for the extracellular domain of human ROR1, such as F(ab)2, Fv, scFv, IgGΔCH$_2$, F(ab')2, scFv2CH3, F(ab), VL, VH, scFv4, scFv3, scFv2, dsFv, Fv, scFv-Fc, (scFv)2, a diabody, and a bivalent antibody. The antibody can be any modified or synthetic antibody, including, but not limited to, non-depleting IgG antibodies, T-bodies, or other Fc or Fab variants of antibodies.

In addition to a heavy chain as described above, the antibody of the invention can further comprise a light chain selected from a Fab library using sequential naive chain shuffling. Likewise, in addition to a light chain as described above, the antibody of the invention can further comprise a heavy chain selected from a Fab library using sequential naive chain shuffling.

In some embodiments, the invention provides an isolated antibody, having specificity for human ROR1, comprising at least one CDR having a sequence selected from the group consisting of SEQ ID NO:4, SEQ ID NO:6, SEQ ID NO:8, SEQ ID NO: 11, SEQ ID NO: 13, and SEQ ID NO: 15. The invention also provides an isolated antibody with specificity for ROR1 comprising at least one or more variants of the foregoing CDR sequences, which include 1, 2, or 3 substitutions, insertions, deletions, or combinations thereof in a sequence selected from the group consisting of SEQ ID NO:4, SEQ ID NO:6, SEQ ID NO:8, SEQ ID NO: 11, SEQ ID NO: 13, and SEQ ID NO: 15. For example, a recombinant chimeric or humanized antibody (or fragment thereof) can include one, two, three, four, five, or all six of the foregoing CDR sequences.

In some embodiments, the invention provides an antibody with avidity for ROR1 of about 10 µM or less, 5 µM or less, 2 µM or less, 1 µM or less, 500 nM or less, 400 nM or less, 300 nM or less, or 200 nM or less. The invention also provides an antibody with avidity for ROR1 of about 100 nM or less, about 75 nM or less, about 50 nM or less, about 25 nM or less, about 10 nM or less, or about 5 nM or less. The invention further provides an antibody with avidity for ROR1 of about 1 nM or less, about 800 pM or less, about 700 pM or less, about 600 pM or less, about 500 pM or less, about 400 pM or less, about 300 pM or less, about 200 pM or less, or about 100 pM or less. Avidity can be measured using art-known techniques, such as ELISA or BIACORE.

The antibody of the invention can be produced by any suitable technique, for example, using any suitable eukaryotic or non-eukaryotic expression system. In certain embodiments, the antibody is produced using a mammalian expression system. In some embodiments, the heavy chain can be encoded by a DNA sequence such as SEQ ID NO: 17 or SEQ ID NO: 18, while the light chain can be encoded by a DNA sequence such as SEQ ID NO: 19 or SEQ ID NO: 20.

The antibody of the invention can be produced using a suitable non-eukaryotic expression system such as a bacterial expression system. Bacterial expression systems can be used to produce fragments such as a F(ab)2, Fv, scFv, IgGΔCH$_2$, F(ab')2, scFv2CH3, F(ab), VL, VH, scFv4, scFv3, scFv2, dsFv, Fv, scFv-Fc, (scFv)2, and diabodies. Techniques for altering DNA coding sequences to produce such fragments are known in the art.

The antibody of the invention can be conjugated to a synthetic molecule using any type of suitable conjugation. Recombinant engineering and incorporated selenocysteine (e.g., as described in International Application Publication WO/2008/122039) can be used to conjugate a synthetic molecule. Other methods of conjugation can include covalent coupling to native or engineered lysine side-chain amines or cysteine side-chain thiols. See, e.g., Wu et al., *Nat. Biotechnol.*, 23: 1137-1146 (2005). The synthetic molecule can be any molecule such as one targeting a tumor. Of course, it will be understood that the synthetic molecule also can be a protein or an antibody.

Synthetic molecules include therapeutic agents such as cytotoxic, cytostatic, or antiangiogenic agents and radioisotopes. A cytotoxic agent can be a plant, fungal, or bacterial molecule (e.g., a protein toxin). A therapeutic agent can be a maytansinoid (e.g., maytansinol or DM1 maytansinoid), a taxane, or a calicheamicin. Therapeutic agents include vincristine and prednisone. A therapeutic agent can be an antimetabolite (e.g., an antifolate such as methotrexate, a fluoropyrimidine such as 5-fluorouracil, cytosine arabinoside, or an analogue of purine or adenosine); an intercalating agent (for example, an anthracycline such as doxorubicin, daunomycin, epirubicin, idarubicin, mitomycin-C, dactinomycin, or mithramycin); a platinum derivative (e.g., cisplatin or carboplatin); an alkylating agent (e.g., nitrogen mustard, melphalan, chlorambucil, busulphan, cyclophosphamide, ifosfamide nitrosoureas or thiotepa); an antimitotic agent (e.g., a vinca alkaloid like vincristine or taxoid such as paclitaxel or docetaxel); a topoisomerase inhibitor (for example, etoposide and teniposide, amsacrine, topotecan); a cell cycle inhibitor (for example, a flavopyridol); or a microbtubule agent (e.g., an epothilone, discodermolide analog, or eleutherobin analog). A therapeutic agent can be a proteosome inhibitor or a topoisomerase inhibitor such as bortezomib, amsacrine, etoposide, etoposide phosphate, teniposide, or doxorubicin. Therapeutic radioisotopes include yttrium ($^{90}$Y), lutetium ($^{177}$Lu), actinium ($^{225}$Ac), praseodymium, astatine ($^{211}$At) rhenium ($^{186}$Re), bismuth ($^{212}$Bi or $^{213}$Bi), and rhodium ($^{188}$Rh). Antiangiogenic agents include linomide, bevacuzimab, angiostatin, and razoxane. The synthetic molecule can be another antibody such as rituximab or bevacuzimab.

A synthetic molecule can also be a label. Labels can be useful in diagnostic applications and can include, for example, contrast agents. A contrast agent can be a radioisotope label such as iodine ($^{131}$I or $^{125}$I) indium ($^{111}$In), technetium ($^{99}$Tc), phosphorus ($^{32}$P), carbon ($^{14}$C), tritium ($^{3}$H), other radioisotope (e.g., a radioactive ion) or a therapeutic radioisotope listed above. Additionally, contrast agents can include radiopaque materials, magnetic resonance imaging (MRI) agents, ultrasound imaging agents, and any other contrast agents suitable for detection by a device that images an animal body. A synthetic molecule can also be a fluorescent label, a biologically active enzyme label, a luminescent label, or a chromophore label.

In some embodiments, the antibody can also have specificity for one or more antigens in addition to ROR1. For example, the antibody of the invention can be engineered (e.g., as a bivalent diabody or a conjugated Fab dimer or trimer) to have specificity for ROR1 and another tumor antigen, e.g., an antigen associated with B-CLL, MCL, Burkett's lymphoma, renal cell carcinoma, colon cancer (e.g., colon adenocarcinoma), or breast cancer (e.g., breast adenocarcinoma). The antibody can be engineered to have specificity for ROR1 and an antigen that promotes activation or targeting of cytotoxic effector cells.

The invention further provides eukaryotic or non-eukaryotic cells that have been recombinantly engineered to produce an antibody of the invention. The eukaryotic or non-eukaryotic cells can be used as an expression system to produce the antibody of the invention. In another embodiment, the invention provides ROR1 targeted immune cells that are engineered to recombinantly express an ROR1 specific antibody of the invention. For example, the invention provides a T-cell engineered to express an antibody of the invention (e.g., an scFv, scFv-Fc, (scFv)2), which is linked to a synthetic molecule with the following domains: a spacer or hinge region (e.g., a CD28, CD28 or IgG hinge), a transmembrane region (e.g., a transmembrane canonical domain), and an intracellular T-cell receptor (TCR) signaling domain, thereby forming a T-body (or chimeric antigen receptor (CAR)). Intracellular TCR signaling domains that can be included in a T-body (or CAR) include, but are not limited to, CD3ζ, FcR-γ, and Syk-PTK signaling domains as well as the CD28, 4-1BB, and CD134 co-signaling domains. Methods for constructing T-cells expressing a T-body (or CAR) are known in the art. See, e.g., Marcu-Malina et al., *Expert Opinion on Biological Therapy.*, Vol. 9, No. 5, posted online Apr. 16 (2009).

The invention provides a method of inhibiting cells that express ROR1 (ROR1 cells) by contacting the cells with an antibody of the invention. The antibody can be a naked (unconjugated) antibody or an antibody conjugated to a synthetic molecule, e.g., a cytotoxic, cytostatic, or antiangiogenic agent or a radioisotope. The method can be used to inhibit ROR1 cells in vitro or in a subject (i.e., in vivo). The contacted ROR1 cells be in, for example, a cell culture or animal model of a disorder associated with elevated levels of ROR1. The method is useful, for example, to measure and/or rank (relative to another antibody) the antibody's inhibitory activity for a specific ROR1 cell type. Inhibiting ROR1 cells can include blocking or reducing the activity or growth of ROR1 cells. Inhibiting can also include the killing of ROR1 cells. While the method is not bound by or limited to any mechanism of action, inhibitory activity can be mediated by blocking ROR1-mediated signaling or by blocking the signaling of an ROR1 associated receptor. Inhibitory activity can also be mediated by recruitment of immune system effectors that attack ROR1 cells, e.g., by activating constituents of the antibody-dependent cell-mediated cytotoxicity (ADCC) or complement systems.

The invention also provides a method of treating a subject that has, is suspected to have, or is at risk for a disorder associated with elevated levels of ROR1. Generally, the method includes administering a therapeutically effective amount of an isolated antibody of the invention to the subject. The antibody can be any anti-ROR1 antibody of the invention as described above. Thus, the antibody can be chimeric, humanized, synthetic, F(ab)2, Fv, scFv, IgGΔCH$_2$, F(ab')2, scFv2CH3, F(ab), VL, VH, scFv4, scFv3, scFv2, dsFv, Fv, or (scFv)2. In some embodiments, the method includes administering an IgG, an scFv, a dsFv, a F(ab')2, a diabody, or a bivalent antibody. The administered antibody can be conjugated to a synthetic molecule described above, e.g., a cytotoxic, cytostatic, or antiangiogenic agent or a therapeutic radioisotope. An exemplary cytotoxic agent is *Pseudomonas exotoxin* A (PE38). Disorders that can be treated include, for example, B-CLL and MCL. Other disorders associated with elevated ROR1 that can be treated include Burkett's lymphoma, renal cell carcinoma, colon cancer (e.g., colon adenocarcinoma), and breast cancer (e.g., breast adenocarcinoma).

The invention also provides a method of treating a subject that has, is suspected to have, or is at risk for a disorder associated with elevated levels of ROR1 by adoptive transfer of the genetically engineered T-cells described herein, which express an antibody of the invention as a T-body (or CAR) that selectively binds ROR1. Recombinant technology can be used to introduce T-body (or CAR) encoding genetic material into any suitable T-cells, e.g., central memory T-cells from the subject to be treated. The T-cells carrying the genetic material can be expanded (e.g., in the presence of cytokines). The genetically engineered T-cells are transferred, typically by infusion, to the patient. The transferred T-cells of the invention can then mount an immune response against ROR1 expressing cells in the subject. The adoptive transfer method can be used, for example, to treat subjects that have or are suspected to have B-CLL, MCL, Burkett's lymphoma, renal cell carcinoma, colon cancer (e.g., colon adenocarcinoma), or breast cancer (e.g., breast adenocarcinoma).

In some embodiments, the foregoing methods of treatment can further include co-administering a second therapeutic agent for the disorder associated with elevated ROR1. For example, when the disorder to be treated involves an ROR1-expressing cancer, the method can further include co-administration of a cytotoxic, cystostatic, or antiangiogenic agent suitable for treating the cancer. If the cancer is a B-cell lymphoma, the method can further include, for example, co-administration of rituximab, alemtuzumab, or a CHOP chemotherapeutic regimen.

The terms "treat," "treating," "treatment," and "therapeutically effective" used herein do not necessarily imply 100% or complete treatment. Rather, there are varying degrees of treatment of which one of ordinary skill in the art recognizes as having a potential benefit or therapeutic effect. In this respect, the inventive method can provide any amount of any level of treatment. Furthermore, the treatment provided by the inventive method can include the treatment of one or more conditions or symptoms of the disease being treated.

In another embodiment, the invention provides method of detecting in a test sample an altered level of ROR1 (e.g., cell surface ROR1), for example, relative to a control. Generally, the method includes contacting an antibody of the invention to the test sample and determining the amount of antibody that selectively binds to material (e.g., cells) in the sample to thereby determine the level of ROR1 in the test sample. A test sample can be from a cell culture or from a test subject, e.g., a plasma or a tissue sample from a subject that has, is suspected to have, or is at risk for a disease or condition associated with elevated ROR1 in a subject. A control level desirably corresponds to the ROR1 level detected using the same antibody in a corresponding sample(s) from one or more control cultures or subjects. Methods of using the antibody of the invention to determine ROR1 levels can include any immunoassay such as immuno- (Western) blotting, enzyme-linked immunosorbent assay (ELISA), and flow cytometry, e.g., fluorescence-activated cell sorting (FACS) analysis.

The method of detection can be used to screen for the presence of a disorder associated with elevated ROR1. The method includes obtaining a sample from a test subject in need of screening, e.g., a subject that has, is suspected to have, or is at risk for a disorder associated with elevated ROR1. The level of ROR1 (e.g., the amount or concentration) in the sample is measured using an antibody of the invention, and the level in the sample is compared to a control level of ROR1. The control level represents, for example, the mean level (e.g., the amount or concentration) in sample(s) from one or, preferably, multiple control group subjects that do not have a disorder associated with elevated ROR1. Alternatively, the control level can correspond to the level or mean level of ROR1 in one or more samples taken from the test subject at one or more prior times, when the test subject did not have or did not exhibit, a condition associated with elevated ROR1. A significantly higher level of ROR1 in the test sample relative to the control level is indicative of a disorder associated with elevated ROR1 in the subject.

In subjects such as humans, where cell surface ROR1 expression is largely restricted to embryonic development, a control level of ROR1 can be zero or none. Thus, in some embodiments of the method of the detection provided by the invention, any significant and detectable amount of ROR1 in a test sample can be indicative of a disorder associated with elevated ROR1 in the subject.

Additionally, the method of detection can be used to monitor the progress of a disorder associated with elevated ROR1. The method includes obtaining a sample from a subject in need of screening, e.g., a subject having been diagnosed or suspected to have a disorder associated with elevated ROR1. The level of ROR1 in the sample is measured using an antibody of the invention, and the level in the sample is compared to a control level corresponding to the level or mean level of ROR1 in one or more samples taken from the test subject at one or more prior times. Levels of ROR1 that are significantly elevated or decreased relative to control indicate that the subject's disorder is deteriorating or improving, respectively.

The foregoing method of detection can be used to screen for the presence or to monitor the progress of disorders including, for example, B-CLL, MCL, Burkett's lymphoma, renal cell carcinoma, colon cancer (e.g., colon adenocarcinoma), and breast cancer (e.g., breast adenocarcinoma).

The invention provides a method for screening a subject for an altered level of ROR1. Generally, the method includes administering to the subject an antibody of the invention that is conjugated to a label (e.g., a contrast agent), imaging the subject in a manner suitable for detecting the label, and determining whether a region in the subject has an altered density or concentration of label as compared to the background level of label in proximal tissue. Alternatively, the method includes determining whether there is an altered density or concentration of label in a region as compared to the density or concentration of label previously detected in the same region of the subject. Methods of imaging a subject can include x-ray imaging, x-ray computed tomography (CT) imaging (e.g., CT angiography (CTA) imaging), magnetic resonance (MR) imaging, magnetic resonance angiography (MRA), nuclear medicine, ultrasound (US) imaging, optical imaging, elastography, infrared imaging, microwave imaging, and the like, as appropriate for detecting the label conjugated to the antibody. In a preferred embodiment, the subject has, is suspected to have, or is at risk for an ROR1-expressing tumor, such as B-CLL, MCL, Burkett's lymphoma, renal cell carcinoma, tumor of the colon (e.g., colon adenocarcinoma), or breast tumor (e.g., breast adenocarcinoma), and the method is used to screen for or detect the presence of the tumor. In another embodiment, the method can be used to monitor the size or density of an ROR1-expressing tumor over time, e.g., during a course of treatment.

The invention also provides a pharmaceutical composition comprising an antibody as described above and a pharmaceutically acceptable carrier. Pharmaceutical compositions can be prepared from any of the antibodies described herein. An exemplary composition includes a chimeric antibody having SEQ ID NO: 1 (heavy chain) and/or SEQ ID NO: 2 (light chain). Another exemplary composition comprises a humanized antibody having one, two, three, four, five, or six CDRs selected from the group consisting of SEQ ID NO:4, SEQ ID NO:6, SEQ ID NO:8, SEQ ID NO: 11, SEQ ID NO: 13, and SEQ ID NO: 15. Still another exemplary pharmaceutical composition includes a dsFv fragment, which comprises the sequence of SEQ ID NO: 1 with a glycine to cysteine substitution at position 44 (heavy chain) and/or the sequence of SEQ ID NO: 2 with a glycine to cysteine substitution at position 100 (light chain).

The composition of the invention comprises a carrier for the antibody, desirably a pharmaceutically acceptable carrier. The pharmaceutically acceptable carrier can be any suitable pharmaceutically acceptable carrier. The term "pharmaceutically acceptable carrier" as used herein means one or more compatible solid or liquid fillers, diluents, other excipients, or encapsulating substances which are suitable for administration into a human or veterinary patient (e.g., a physiologically acceptable carrier or a pharmacologically acceptable carrier). The term "carrier" denotes an organic or inorganic ingredient, natural or synthetic, with which the active ingredient is combined to facilitate the application. The pharmaceutically acceptable carrier can be co-mingled with one or more of the active components, e.g., a hybrid molecule, and with each other, when more than one pharmaceutically acceptable carrier is present in the composition in a manner so as not to substantially impair the desired pharmaceutical efficacy. "Pharmaceutically acceptable" materials typically are capable of administration to a patient without the production of significant undesirable physiological effects such as nausea, dizziness, rash, or gastric upset. It is, for example, desirable for a composition comprising a pharmaceutically acceptable carrier not to be immunogenic when administered to a human patient for therapeutic purposes.

The pharmaceutical composition can contain suitable buffering agents, including, for example, acetic acid in a salt, citric acid in a salt, boric acid in a salt, and phosphoric acid in a salt. The pharmaceutical compositions also optionally can contain suitable preservatives, such as benzalkonium chloride, chlorobutanol, parabens, and thimerosal.

The pharmaceutical composition can be presented in unit dosage form and can be prepared by any suitable method, many of which are well known in the art of pharmacy. Such methods include the step of bringing the antibody of the invention into association with a carrier that constitutes one or more accessory ingredients. In general, the composition is prepared by uniformly and intimately bringing the active agent into association with a liquid carrier, a finely divided solid carrier, or both, and then, if necessary, shaping the product.

A composition suitable for parenteral administration conveniently comprises a sterile aqueous preparation of the inventive composition, which preferably is isotonic with the blood of the recipient. This aqueous preparation can be formulated according to known methods using suitable dispersing or wetting agents and suspending agents. The sterile injectable preparation also can be a sterile injectable solution or suspension in a non-toxic parenterally-acceptable diluent or solvent, for example, as a solution in 1,3-butane diol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed, such as synthetic mono-or di-glycerides. In addition, fatty acids such as oleic acid can be used in the preparation of injectables. Carrier formulations suitable for oral, subcutaneous, intravenous, intramuscular, etc. administrations can be found in *Remington's Pharmaceutical Sciences*, Mack Publishing Co., Easton, Pa.

The delivery systems useful in the context of the invention include time-released, delayed release, and sustained release delivery systems such that the delivery of the inventive composition occurs prior to, and with sufficient time to cause, sensitization of the site to be treated. The inventive composition can be used in conjunction with other therapeutic agents or therapies. Such systems can avoid repeated administrations of the inventive composition, thereby increasing convenience to the subject and the physician, and may be particularly suitable for certain compositions of the invention.

Many types of release delivery systems are available and known to those of ordinary skill in the art. Suitable release delivery systems include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are lipids including sterols such as cholesterol, cholesterol esters, and fatty acids or neutral fats such as mono-di-and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which the active composition is contained in a form within a matrix such as those described in U.S. Pat. Nos. 4,452,775, 4,667,014, 4,748,034, and 5,239,660 and (b) diffusional systems in which an active component permeates at a controlled rate from a polymer such as described in U.S. Pat. Nos. 3,832,253 and 3,854,480. In addition, pump-based hardware delivery systems can be used, some of which are adapted for implantation.

The term "subject" is used herein, for example, in connection with therapeutic and diagnostic methods, to refer to human or animal subjects. Animal subjects include, but are not limited to, animal models, such as, mammalian models of conditions or disorders associated with elevated ROR1 expression such as B-CLL, MCL, Burkett's lymphoma, renal cell carcinoma, colon cancer, (e.g., colon adenocarcinoma), and breast cancer (e.g., breast adenocarcinoma).

The invention also provides kits suitable for carrying out the methods of the invention. Typically, a kit comprises two or more components required for performing a therapeutic or detection method of the invention. Kit components include, but are not limited to, one or more antibody of the invention, appropriate reagents, and/or equipment.

A kit can comprise an antibody of the invention and an immunoassay buffer suitable for detecting ROR1 (e.g. by ELISA or FACS). The kit may also contain one or more microliter plates, standards, assay diluents, wash buffers, adhesive plate covers, and/or instructions for carrying out a method of the invention using the kit. The kit can include an antibody of the invention bound to a substrate (e.g., a multi-well plate or a chip), which is suitably packaged and useful to detect ROR1. In some embodiments, the kit includes an antibody of the invention that is conjugated to a label, such as, a fluorescent label, a biologically active enzyme label, a luminescent label, or a chromophore label. The kit can further include reagents for visualizing the conjugated antibody, e.g., a substrate for the enzyme. In some embodiments, the kit includes an antibody of the invention that is conjugated to a contrast agent and, optionally, one or more reagents or pieces of equipment useful for imaging the antibody in a subject.

Generally the antibody of the invention in a kit is suitably packaged, e.g., in a vial, pouch, ampoule, and/or any container appropriate for a therapeutic or detection method. Kit components can be provided as concentrates (including lyophilized compositions), which may be further diluted prior to use or they can be provided at the concentration of use. When the antibody of the invention for use in vivo, single dosages may be provided in sterilized containers having the desired amount and concentration of agents.

The following examples further illustrate the invention but, of course, should not be construed as in any way limiting its scope.

EXAMPLE 1

This example demonstrates the preparation of monoclonal antibodies with specificity for ROR1.

Figure 1:
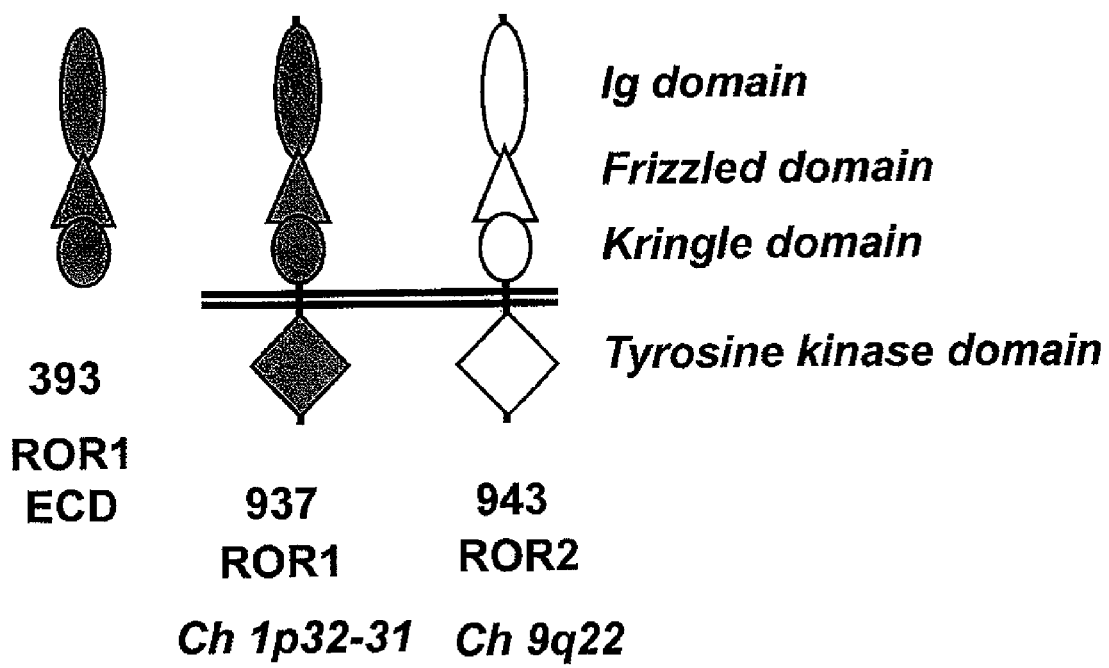
FIG. 1 is a schematic that depicts the Ig-, Frizzled-, and Kringle-like domains of ROR1, receptor tyrosine kinase-like orphan receptor 2 (ROR2), and an ROR1-derived extracellular domain fragment (ROR1-ECD), as well as the transmembrane and intracellular tyrosine kinase domains of ROR1 and ROR2.
Figure 2A:
FIG. 2A is a schematic that depicts ROR-ECD.
Figure 2B:
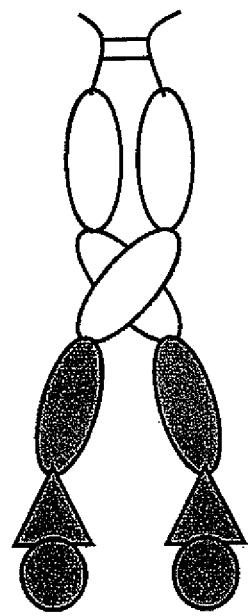
FIG. 2B is a schematic that depicts ROR1-ECD fused to a human Fc domain (Fc-ROR1).

Mice were immunized with a fusion protein consisting of the human Fc domain and extracellular domain of human ROR1 (Fc-ROR1). As depicted in FIG. 1, the extracellular domain of ROR1 includes an immunoglobulin (Ig) domain, a Frizzled domain, and a Kringle domain, which span about 393 amino acids of the amino-terminal portion of ROR1. A nucleic acid sequence encoding the ROR1 extracellular domain was recombinantly linked to a nucleic acid sequence encoding human Fc1 to form a recombinant construct that then was expressed in HEK 293 cells. The produced Fc-ROR1 fusion protein (depicted in FIG. 2B) was harvested and purified by ion exchange chromatography and gel filtration or by Protein A affinity chromatography. The results of a Coomassie-stained protein gel analysis of purified Fc-ROR1 under non-reducing and reducing conditions are shown in FIG. 2C.

Mice were immunized with the Fc-ROR1, and antibody-producing cells were immortalized to produce hybridomas. Supernatants from twenty hybridomas were screened for specific ROR1 binding. An ELISA plate was coated with human ROR1-ECD (50 ng per well overnight at 4° C.), then blocked with 3% BSA-PBS (room temperature for 2 hours), and subsequently contacted with dilutions of affinity purified of mouse mAb (room temperature for 2 hours). After washing (with PBS-Tween 20), horseradish peroxidase (HRP)-conjugated goat anti-mouse (1:2000 dilution) was added (1 hour at room temperature) and washed. The bound antibody was detected using the peroxidase substrate ABTS (2,2'-azino-bis (3-ethylbenzthiazoline-6-sulfonic acid). Four monoclonal antibodies (mAb 2A2, 2D11, 1A1, and 1A7) were identified by ELISA as specifically binding ROR1.

The four specific mAbs were further characterized as IgG using goat anti-human IgG polyclonal antibodies (pAbs) conjugated to HRP. Flow cytometry was used to evaluate the ability of each of the four antibodies to bind to cells expressing ROR1. The mAb 2A2 antibody was also further characterized by surface plasmon resonance (BIACORE, GE Healthcare, Piscataway, N.J.). The results of the foregoing experiments and also the antibody expression yield for two hybridomas are summarized in Table 1.

TABLE 1

| mAb | Isotype | ELISA | Flow Cytometry | BIACORE | mAb Expression |
|---|---|---|---|---|---|
| 2A2 | mouse IgG1κ | +++ | +++ | +++ | 10 mg/L |
| 2D11 | mouse IgG1κ | ++ | ++ | not determined | 23 mg/L |
| 1A1 | mouse IgG1κ | ++ | + | not determined | not determined |
| 1A7 | mouse IgG1κ | ++ | + | not determined | not determined |

The foregoing results demonstrate the isolation of four mAbs with specificity for the extracellular domain of human ROR1.

EXAMPLE 2

This example further demonstrates the desirable binding properties of mAb 2A2 for ROR1.

Hybridoma 2A2 of Example 1 was grown in CELLINE Disposable Bioreactors (BD Biosciences, San Jose, Calif.) using animal component-free BD Cell MAb Medium. Expressed mAb 2A2 was purified by Protein G affinity chromatography.

Figure 3:
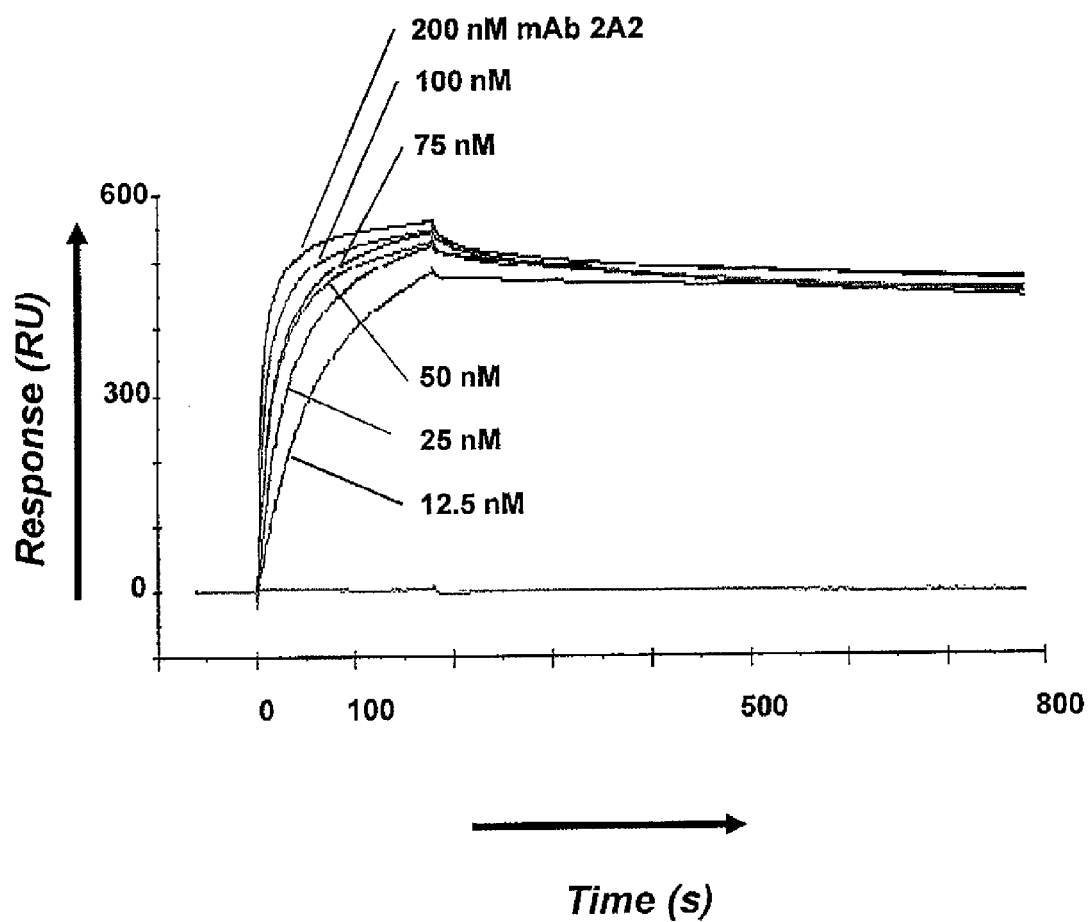
FIG. 3 is a graph depicting the results of a BIACORE binding analysis using the indicated concentrations of mouse monoclonal antibody (mAb) 2A2 in terms of response (RU) versus time (seconds).

The avidity of mAb 2A2 for ROR1-ECD was determined using surface plasmon resonance in a BIACORE X100 instrument (GE Healthcare, Piscataway, N.J.). Human ROR1-ECD was coupled to a BIACORE CM5 chip at 1600 resonance units. MAb 2A2 was diluted in HBS-EP buffer (0.01 M HEPES, 0.15 M NaCl, 3 mM EDTA, and 0.005% surfactant P20, pH 7.4; GE Healthcare) to various concentrations (from about 200 nM to about 12.5 nM) and injected sequentially. As depicted by the extended, flat tail in FIG. 3, antibody binding was very stable at all concentrations tested. Association (k-on) and dissociation (k-off) rate constants were calculated based on a 1:1 Langmuir binding model using BIAEVALUATION software (GE Healthcare). The equilibrium dissociation constant (Kd=k-off/k-on) was calculated, and the avidity of mAb 2A2 was determined to be 100 pM.

Fluorescence-activated cell sorting (FACS) analysis was performed to test the ability of mAb 2A2 to bind to peripheral blood mononuclear cells (PBMC) from normal patients, to PBMC from a B-CLL patient, and to the human ROR1-expressing MCL cell line JeKo-1. Antibody binding was detected using goat anti-mouse IgG polyclonal antibody conjugated to fluorescein isothiocyanate (FITC). Results for antibody concentrations of from about 0.001 μg/ML to about 1 μg/mL (about 6.5 pM to about 6.5 nM), secondary antibody alone, and polyclonal mouse IgG control are depicted in the histograms of FIG. 4. Control mouse IgG (black-filled histogram) did not show a significant shift relative to secondary antibody alone (broken line histogram). mAb 2A2 did exhibit significant binding to JeKo-1 (FIG. 4, second panel) and to primary B-CLL cells present in the PBMC sample from a representative patient (FIG. 4, first panel). Binding to each of these cell populations was observed using mAb 2A2 concentrations as low as 1 ng/mL and 10 ng/mL, respectively (see FIG. 4).

Similar FACS analyses of mAb 2A2 binding to normal B cells from healthy donors were negative.

The foregoing results demonstrate that mAb 2A2 has good avidity for its antigen and can be used to specifically distinguish (i) tumor cells obtained from lymphoma patients from (ii) normal B-cells taken from healthy subjects.

EXAMPLE 3

This example demonstrates the identification of mAb 2A2 variable domain coding and amino acid sequences.

The variable domain encoding sequences of heavy (VH) and light (VL) chain of mAb 2A2 were RT-PCR amplified from hybridoma 2A2 total RNA using published primer sequences (Morrison, S. L., in *Curent Protocols in Immunology*, Suppl. 47, pp. 2.12.1-2.12.17, John Wiley and Sons, 2002). The cDNAs were cloned and analyzed by DNA sequencing. VH and VL chain sequences were independently confirmed by liquid chromatography-tandem mass spectrometry (LC-MS/MS) analysis of the tryptic digests of the heavy and light chain polypeptides, which were resolved by sodium dodecyl sulfate polyacrylamide gel electrophoresis (SDS-PAGE). The amino acid sequences and cDNA sequences of the VH and VL chains of mAb 2A2 are depicted in FIGS. 5 and 6 ("original sequences"), respectively.

EXAMPLE 4

This example demonstrates the construction and characterization of a chimeric human-mouse antibody with desirable binding properties for ROR1.

Codon optimization of mAb 2A2 VH and VL DNA sequences (SEQ ID NO: 17 and SEQ ID NO: 19, respectively) produced the sequences of SEQ ID NO: 18 and SEQ ID NO: 20, respectively, which are depicted in FIG. 6. Optimized sequences were used to generate a chimeric antibody vector, generally according to the method described in Morrison, S. L., in *Curent Protocols in Immunology*, Coligan et al. Eds., Suppl. 47, pp. 2.12.1-2.12.17, John Wiley and Sons, 2002. The optimized VH and VL sequences as well as human CκL segments were cloned into the pIgG mammalian expression vector which is described in Rader et al., *FASEB J.*, 16:2000-2002 (2002). The resulting plasmids were transfected and expressed in HEK 293F cells to produce chimeric mouse/human 2A2 IgG1 (ch2A2) as described in Hofer et al., *J. Immunol. Methods*, 318: 75-87 (2007). The chimeric ch2A2 antibody is schematically depicted in FIG. 7A with mouse and human antibody domains shown by light and dark fills, respectively.

Ch2A2 and mouse mAb 2A2 were evaluated by ELISA for their ability to bind to ROR1-ECD and a commercial ROR2-Fc (R&D Systems, Minneapolis, Minn.). ELISA was performed as described in Example 1, with chimeric ch2A2 being detected using HRP-conjugated goat anti-human kappa antibody. ELISA results are depicted in FIG. 7B. While neither ch2A2 nor mAb 2A2 bound to the ROR2-Fc control, ch2A2 retained virtually all of the mAb 2A2 binding affinity for the extraceullar domain of ROR1 (see FIG. 7B).

Ch2A2 was also compared to mAb 2A2 by FACS for its ability to bind to the human ROR1-expressing MCL cell line JeKo-1 and to PBMC from B-CLL patients. A FACS analysis was carried out as described in Example 2 above, except that mAb 2A2 (1 µg/ml) and ch2A2 (1 µg/ml) were detected using allophycocyanin (APC) conjugated goat anti-mouse IgG (Fe) and APC conjugated goat anti-human IgG (Fc), respectively. The results of the FACS analysis for JeKo-1 cells are depicted in FIG. 8. Control mouse IgG did not show a significant shift relative to secondary antibody alone (black-filled histogram). The results indicate that mAb 2A2 and ch2A2 at 1 µg/ml similarly bind to JeKo-1 (see FIG. 8).

Similar results were obtained by FACS analysis comparing mAb 2A2 and ch2A2 binding to PBMC from B-CLL patients.

The foregoing data demonstrate the generation of chimeric mouse/human antibody of the invention with conserved specificity and affinity for the extracellular domain of ROR1, including native ROR1 expressed on the cell surface of malignant B-cells.

EXAMPLE 5

This example demonstrates the construction and characterization of a disulfide stabilized fragment (dsFv) of mAb 2A2 fused to an immunotoxin.

A dsFv fragment of mAb 2A2 (dsFv 2A2) was generated and fused to a 38-kDa fragment of *Pseudomonas* exotoxin A (PE38) generally according to methods described in Pastan et al., *Methods Mol. Biol.*, 248: 503-518 (2004). The original VH and VL coding sequences of mAb 2A2 (see FIG. 6) were altered to introduce a glycine to cysteine substitution at positions 44 and 100 of SEQ ID NO: 1 and SEQ ID NO: 2, respectively (substituted residues are underlined in FIG. 5). The altered VH coding sequence was subcloned in-frame with a PE38 coding sequence in a pRB98 vector carrying a chloramphenicol resistance gene (the vector is described in Kreitman et al., in *Drug Targeting*, Francis et al., Eds., Vol. 25, pp. 215-226, Humana Press Inc, Totowa, N.J., 2000). Altered VH and VL chains were separately expressed in *E. coli*, and the resulting proteins were harvested and solubilized. The VH and VL were refolded together to form dsFv 2A2-PE38 fusion immunotoxin, which was purified by Q-Sepharose ion-exchange chromatography as described in Pastan et al., supra, 2004.

Recombinant dsFv 2A2-PE38 immunotoxin was evaluated by flow cytometry and compared to mouse mAb 2A2 for its ability to bind to the human ROR1-expressing mantle cell lymphoma cell line JeKo-1. JeKo-1 cell binding by mAb 2A2 was detected using a goat anti-mouse IgG polyclonal antibody (pAb) conjugated to APC (Jackson ImmunoResearch Laboratories, West Grove, Pa.) at 1:300 dilution. JeKo-1 cell binding of dsFv 2A2-PE38 was detected using rabbit anti-*Pseudomonas* exotoxin A pAb (1:100 dilution) (Sigma-Aldrich, St. Louis, Mo.) as a secondary antibody and goat anti-rabbit IgG pAb conjugated to Cy5 (1:300 dilution) (Jackson ImmunoResearch Laboratories) as a tertiary antibody. Flow cytometry results are depicted in FIG. 9A. The results demonstrate that, despite the inherent monovalency of the recombinant dsFv 2A2-PE38 immunotoxin, its binding to native cell surface ROR1 was detectable at concentrations of less than 1 µg/mL (FIG. 9).

An analysis of dsFv 2A2-PE38 immunotoxin binding to PBMC from B-CLL patients showed similar results. Additionally, ELISA experiments demonstrated that dsFv 2A2-PE38 immunotoxin retains binding specificity for the extracellular domain of human ROR1.

The foregoing example provides a recombinant immunotoxin conjugated antibody of the invention, which is based on mAb 2A2 and which has conserved binding specificity for ROR1, including native ROR1 expressed on the cell surface of malignant B-cells.

EXAMPLE 6

This example demonstrates dsFv 2A2-PE38 mediated cytotoxicity of ROR1 expressing cells.

JeKo-1 cells were cultured in Roswell Park Memorial Institute (RPMI) 1640 medium supplemented with 10% fetal calf serum and incubated for 51 hours at 37° C. in a 96-well tissue culture plate with various doses (0-100 µ/mL) of the dsFv 2A2-PE38 immunotoxin prepared in Example 5. The cells were subsequently analyzed by flow cytometry using annexin V and propidium iodide to stain apoptotic and dead cells, respectively. The percentage of cells that were positive for both annexin V and propidium iodide is shown as cytotoxicity on the y-axis, as a function of the concentration of dsFv 2A2-PE38, of FIG. 10. FIG. 11 further demonstrates that the cytotoxicity of dsFv 2A2-PE38 (2 μM) included not only cell death (necrosis) as evidenced by propidium iodide staining, but also extensive apoptosis, as evidenced by annexin V staining.

The data confirmed the ability of dsFv 2A2-PE38 to effect dose-dependent killing of JeKo-1 cells at microgram concentrations or less.

EXAMPLE 7

This example demonstrates epitope mapping of the interaction between mAb 2A2 and ROR1 using ELISA.

Recombinant proteins containing one, two, or three of the three extracellular domains of human ROR1 (d1-Ig, d2-Frizzled, and d3-Kringle) as shown in FIG. 12 were coated on an ELISA plate. Each of the proteins was genetically fused to a human Fc region; a protein containing the three extracellular domains without the Fc region was also prepared. Cross-reactivity to mouse ROR1 was determined by coating recombinant Fc-mouse ROR1 protein on the ELISA plate. Binding of mouse mAb 2A2 to the different ROR1 proteins was detected using HRP-conjugated donkey anti-mouse IgG polyclonal antibodies. The reactivity was scored "++" for strong binding, "+" for moderate binding, and "−" for no detectable binding. As shown in FIG. 12, strong binding was detected for Fc-hROR1, which contained all three extracellular domains, as well as hROR1ECD, which contained the extracellular domains without an Fc region, and Fc-hROR1 (d1d2), which contained the Ig and Frizzled domains. Moderate binding was detected for Fc-hROR(d1), which contained the Ig domain only. No binding was detected for Fc-hROR1(d2d3), Fc-hROR1(d2), or Fc-hROR(d3).

These results show that the binding epitope for the 2A2-ROR1 interaction is likely in the Ig domain, but is assisted either directly or indirectly by the Frizzled domain of ROR1.

The foregoing results demonstrate the dose-dependent killing of ROR1 expressing cells by an immunotoxin-conjugated antibody of the invention.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. An antibody having specificity for the extracellular domain of human receptor tyrosine kinase-like orphan receptor 1 (ROR1), comprising complementarity determining regions (CDRs) with the following sequences: SEQ ID NO: 4, SEQ ID NO: 6, SEQ ID NO: 8, SEQ ID NO: 11, SEQ ID NO: 13, and SEQ ID NO: 15.

2. The antibody of claim 1, wherein the antibody comprises:
   (a) a heavy chain variable domain having at least 95% sequence identity to the amino acid sequence of SEQ ID NO: 1; and
   (b) a light chain variable domain having at least 95% sequence identity to the amino acid sequence of SEQ ID NO: 2.

3. The antibody of claim 2, wherein the heavy chain variable domain comprises the amino acid sequence of SEQ ID NO: 1.

4. The antibody of claim 2, wherein the heavy chain variable domain has a sequence comprises the amino acid sequence of SEQ ID NO: 1 with a glycine to cysteine substitution at position 44.

5. The antibody of claim 2, wherein the light chain variable domain consists of the amino acid sequence of SEQ ID NO: 2.

6. The antibody of claim 2, wherein the light chain variable domain comprises the amino acid sequence of SEQ ID NO: 2 with a glycine to cysteine substitution at position 100.

7. The antibody of claim 2, wherein the heavy chain variable domain comprises the amino acid sequence of SEQ ID NO: 1 and the light chain variable domain comprises the amino acid sequence of SEQ ID NO: 2.

8. The antibody of claim 2, wherein the heavy chain variable domain comprises the amino acid sequence of SEQ ID NO: 1 with a glycine to cysteine substitution at position 44, and the light chain variable domain comprises the amino acid sequence of SEQ ID NO: 2 with a glycine to cysteine substitution at position 100.

9. The antibody of claim 1, wherein the antibody is selected from the group consisting of IgA1, IgA2, IgD, IgE, IgG1, IgG2, IgG3, IgG4, IgM, F(ab)2, Fv, scFv, IgGΔCH2, F(ab')2, scFv2CH3, F(ab), VL, VH, scFv4, scFv3, scFv2, dsFv, Fv, scFv-Fc, (scFv)2, a non-depleting IgG, a diabody, and a bivalent antibody.

10. The antibody of claim 9, wherein the antibody is an IgG selected from the group consisting of IgG1, IgG2, IgG3, IgG4, and synthetic IgG.

11. The antibody of claim 9, wherein the antibody is a Fab.

12. The antibody of claim 9, wherein the antibody is a dsFv.

13. The antibody of claim 1, wherein the antibody is conjugated to a synthetic molecule.

14. The antibody of claim 13, wherein the antibody is a T-body and the synthetic molecule comprises a transmembrane region and an intracellular T-cell receptor (TCR) signaling domain.

15. The antibody of claim 13, wherein the synthetic molecule is a label.

16. The antibody of claim 13, wherein the synthetic molecule is a cytotoxic agent or a therapeutic radioisotope.

17. A pharmaceutical composition comprising a therapeutically effective amount of an antibody of claim 2 and a pharmaceutically acceptable carrier.

18. A kit comprising the antibody of claim 2.

19. The kit of claim 18, further comprising one or more immunoassay buffers.

20. The kit of claim 18, wherein the antibody is conjugated to a label.

21. A pharmaceutical composition comprising a therapeutically effective amount of an antibody of claim 1 and a pharmaceutically acceptable carrier.

22. A kit comprising the antibody of claim 1.

23. A conjugate comprising the antibody of claim 2 and a cytotoxic agent.

24. The conjugate of claim 23, wherein the cytotoxic agent is *Pseudomonas* exotoxin A (PE38).

25. A conjugate comprising the antibody of claim 1 and a cytotoxic agent.

26. The conjugate of claim 25, wherein the cytotoxic agent is *Pseudomonas* exotoxin A (PE38).

27. The antibody of claim 2, wherein the antibody has specificity for one or more antigens in addition to ROR1.

28. The antibody of claim 27, wherein the one or more antigens is a tumor antigen.

29. The antibody of claim 27, wherein the one or more antigens is an antigen that promotes activation or targeting of cytotoxic effector cells.

30. The antibody of claim 1, wherein the antibody has specificity for one or more antigens in addition to ROR1.

31. The antibody of claim 30, wherein the one or more antigens is a tumor antigen.

32. The antibody of claim 30, wherein the one or more antigens is an antigen that promotes activation or targeting of cytotoxic effector cells.

\* \* \* \* \*